United States Patent
Ding et al.

(10) Patent No.: US 12,168,806 B2
(45) Date of Patent: Dec. 17, 2024

(54) FULL-AUTOMATIC DETECTION APPARATUS AND SYSTEM FOR IMPORTANT ZOONOTIC PATHOGEN, AND CONTROL METHOD FOR FULL-AUTOMATIC DETECTION APPARATUS FOR IMPORTANT ZOONOTIC PATHOGEN

(71) Applicant: Institute of Animal Sciences, Chinese Academy of Agricultural Sciences, Beijing (CN)

(72) Inventors: Jiabo Ding, Beijing (CN); Xiaowen Yang, Beijing (CN); Hui Jiang, Beijing (CN); Lin Liang, Beijing (CN); Ting Xin, Beijing (CN); Guangzhi Zhang, Beijing (CN); Xuezheng Fan, Beijing (CN); Qingchun Shen, Beijing (CN)

(73) Assignee: Institute of Animal Sciences, Chinese Academy of Agricultural Sciences, Beijing (CN)

( * ) Notice: Subject to any disclaimer, the term of this patent is extended or adjusted under 35 U.S.C. 154(b) by 0 days.

(21) Appl. No.: 18/456,540

(22) Filed: Aug. 28, 2023

(65) Prior Publication Data
US 2024/0068056 A1    Feb. 29, 2024

(30) Foreign Application Priority Data
Aug. 30, 2022    (CN) .................. 202211049188.X

(51) Int. Cl.
*C12Q 1/70*    (2006.01)
*C12Q 1/689*    (2018.01)
(Continued)

(52) U.S. Cl.
CPC ............. *C12Q 1/701* (2013.01); *C12Q 1/689* (2013.01); *G01N 1/2205* (2013.01);
(Continued)

(58) Field of Classification Search
None
See application file for complete search history.

(56) References Cited

U.S. PATENT DOCUMENTS 11,300,484 B1 *    4/2022    Bango .................. H01J 49/027
11,519,040 B2 *    12/2022    Molyneux ................ A61L 2/24
(Continued)

FOREIGN PATENT DOCUMENTS

| CN | 112501258 A | 3/2021 |
| CN | 112631282 A | 4/2021 |

(Continued)

OTHER PUBLICATIONS

CNIPA, Notification of Second Office Action for CN202211049188.X, Dec. 15, 2023.
(Continued)

*Primary Examiner* — Brian R Gordon
(74) *Attorney, Agent, or Firm* — Hemisphere Law, PLLC; Zhigang Ma

(57) ABSTRACT

A full-automatic detection apparatus and system for important zoonotic pathogen, and a control method therefor. The full-automatic detection apparatus for important zoonotic pathogen includes: a base capable of moving; an air collection device, configured to collect a to-be-detected sample in air along with the movement of the base; a nucleic acid detection and analysis device, configured to detect the to-be-detected sample collected by the air collection device to determine whether an infectious pathogen exists in the to-be-detected sample; an intelligent mobile device, configured to plan and control a moving path of the base; and a control device, configured to control the intelligent mobile device to plan and control the moving path of the base and to control a sampling period of the air collection device according to a control instruction of the terminal, and (Continued)

transmit a detection result from the nucleic acid detection and analysis device to the terminal.

3 Claims, 2 Drawing Sheets

(51) Int. Cl.
*G01N 1/22* (2006.01)
*G01N 33/00* (2006.01)
*C12Q 1/6851* (2018.01)

(52) U.S. Cl.
CPC ..... *G01N 33/0011* (2013.01); *G01N 33/0073* (2013.01); *C12Q 1/6851* (2013.01)

(56) References Cited

U.S. PATENT DOCUMENTS

| | | | | |
|---|---|---|---|---|
| 11,555,764 | B1* | 1/2023 | Srikrishna | C12Q 1/6869 |
| 2004/0260470 | A1* | 12/2004 | Rast | G06Q 10/0637 |
| | | | | 705/337 |
| 2015/0247187 | A1* | 9/2015 | Bermpohl | C12Q 1/686 |
| | | | | 435/6.12 |
| 2016/0025603 | A1* | 1/2016 | Kindt | G01N 33/56983 |
| | | | | 422/534 |
| 2017/0323481 | A1* | 11/2017 | Tran | H04N 23/611 |
| 2018/0311515 | A1* | 11/2018 | Wilson | A61B 5/6803 |
| 2021/0136722 | A1* | 5/2021 | Scialò | G01N 1/02 |
| 2021/0324485 | A1* | 10/2021 | Hodges | C12Q 1/701 |
| 2022/0177981 | A1* | 6/2022 | Hodges | C12Q 1/6825 |
| 2023/0027503 | A1* | 1/2023 | Liu | G01N 1/2205 |
| 2023/0408380 | A1* | 12/2023 | Maggio | G01N 1/2273 |

FOREIGN PATENT DOCUMENTS

| | | |
|---|---|---|
| CN | 113502221 A | 10/2021 |
| CN | 114736782 A | 7/2022 |

OTHER PUBLICATIONS

Institute of Animal Husbandry, Chinese Academy of Agricultural Sciences (Applicant), Supplemental Reply to Notification of Second Office Action for CN202211049188.X, w/ (allowed) replacement claims, Feb. 1, 2024.

CNIPA, Notification to grant patent right for invention in CN202211049188.X, Feb. 6, 2024.

* cited by examiner

```
                                                    ┌─ 100
┌─────────────────────────────────────────────────────────────────────────┐
│ receiving a control instruction from a terminal, the control instruction includes an infectious pathogen │
│            type, an infectious pathogen detection area and a detection period            │
└─────────────────────────────────────────────────────────────────────────┘
                                      │
                                      ▼                             ┌─ 200
┌─────────────────────────────────────────────────────────────────────────┐
│ determining a sampling mode and a nucleic acid detection mode according to the infectious pathogen │
│                                    type                                 │
└─────────────────────────────────────────────────────────────────────────┘
                                      │
                                      ▼                             ┌─ 300
┌─────────────────────────────────────────────────────────────────────────┐
│   planning a target moving path and a target detection path according to the infectious pathogen │
│                                detection area                           │
└─────────────────────────────────────────────────────────────────────────┘
                                      │
                                      ▼                             ┌─ 400
┌─────────────────────────────────────────────────────────────────────────┐
│   controlling the full-automatic detection apparatus for important zoonotic pathogen to move to the │
│             infectious pathogen detection area along the target moving path            │
└─────────────────────────────────────────────────────────────────────────┘
                                      │
                                      ▼                             ┌─ 500
┌─────────────────────────────────────────────────────────────────────────┐
│   controlling the full-automatic detection apparatus for important zoonotic pathogen to move in the │
│  infectious pathogen detection area along the target detection path according to the detection period, │
│    and simultaneously controlling the automatic detection apparatus for important zoonotic pathogen to │
│                         collect air according to the sampling mode      │
└─────────────────────────────────────────────────────────────────────────┘
                                      │
                                      ▼                             ┌─ 600
┌─────────────────────────────────────────────────────────────────────────┐
│  after the full-automatic detection apparatus for important zoonotic pathogen collects the air for the │
│  detection period, collecting a to-be-detected sample and performing nucleic acid detection on the to- │
│                    be-detected sample according to the nucleic acid detection mode     │
└─────────────────────────────────────────────────────────────────────────┘
                                      │
                                      ▼                             ┌─ 700
┌─────────────────────────────────────────────────────────────────────────┐
│        after the nucleic acid detection is completed, uploading nucleic acid detection data to the terminal │
└─────────────────────────────────────────────────────────────────────────┘
```

FIG. 2

FULL-AUTOMATIC DETECTION APPARATUS AND SYSTEM FOR IMPORTANT ZOONOTIC PATHOGEN, AND CONTROL METHOD FOR FULL-AUTOMATIC DETECTION APPARATUS FOR IMPORTANT ZOONOTIC PATHOGEN

TECHNICAL FIELD

The disclosure relates to the technical field of biotechnologies, particularly to a full-automatic detection apparatus and system for important zoonotic pathogen, and a control method for full-automatic detection apparatus for important zoonotic pathogen.

BACKGROUND

The risk warning of infectious diseases, especially zoonotic pathogens, has always been a hot and difficult point in the prevention and control of infectious diseases, whether in human residential areas or livestock breeding places. The current situation demonstrates that it is necessary to strengthen the detection and prevention of the infectious diseases. Real-time monitoring and effective risk early warning are helpful to the prevention and control of animal diseases and even purification, can move forward the prevention and control of zoonotic diseases, find hidden dangers early, and finally help to realize "One Health".

SUMMARY

The disclosure provides a full-automatic detection apparatus and system for important zoonotic pathogen, and a control method for full-automatic detection apparatus for important zoonotic pathogen, which are used to solve the problems in the related art that a detection process of infectious diseases in residents' epidemic prevention areas or livestock farms is complicated, and the early warning of infectious diseases is not timely.

In a first aspect, the disclosure provides a full-automatic detection apparatus for important zoonotic pathogen, which includes:
  a base capable of moving;
  an air collection device, arranged on the base and configured to collect a to-be-detected sample in air along with the movement of the base;
  a nucleic acid detection and analysis device, arranged on the base and configured to detect the to-be-detected sample collected by the air collection device to determine whether an infectious pathogen exists in the to-be-detected sample;
  an intelligent mobile device, arranged on the base and electrically connected to the base, and configured to plan and control a moving path of the base; and
  a control device, where the control device is configured for communication connection with a terminal and is electrically connected to the intelligent mobile device, the nucleic acid detection and analysis device and the air collection device, and the control device is configured to control the intelligent mobile device to plan and control the moving path of the base and to control a sampling period of the air collection device according to a control instruction of the terminal, and is configured to transmit a detection result from the nucleic acid detection and analysis device to the terminal.

In an embodiment, the air collection device includes: an air compressor, configured to extract the air along with the movement of the base; a filter membrane, configured to filter the air; and an elution instrument, configured to clean the filter membrane by using a sampling medium and collect the to-be-detected sample.

In an embodiment, the filter membrane is at least two in number, filter holes of the at least two filter membranes have different sizes, and the at least two filter membranes are configured to correspondingly filter at least two selected from the group consisting of bacteria, molds, fungi, viruses and spores in the air.

In an embodiment, the intelligent mobile device includes a navigation device, an obstacle detection device and a camera, the navigation device is configured to plan the moving path of the base according to the control instruction, and the obstacle detection device is configured to detect an obstacle in the moving path and control the base to avoid the obstacle.

In an embodiment, the nucleic acid detection and analysis device includes a thermal inactivation and cracking module, a concentration module and a nucleic acid detection module; and the thermal inactivation and cracking module is configured to inactivate and crack bacteria or viruses in the to-be-detected sample, the concentration module is configured to concentrate the to-be-detected sample, and the nucleic acid detection module is configured to detect and determine whether the infectious pathogen exists in the to-be-detected sample.

In an embodiment, the nucleic acid detection module is at least two in number, and detection methods used by the at least two nucleic acid detection modules include fluorescence quantification, loop-mediated isothermal amplification reaction, strand displacement isothermal amplification reaction, rolling loop amplification reaction, cross primer amplification, or recombinant polymerase isothermal amplification reaction.

In a second aspect, the disclosure provides a full-automatic detection system for important zoonotic pathogen, which includes:
  a terminal; and
  at least one full-automatic detection apparatus for important zoonotic pathogen as described above, which is electrically connected to the terminal.

In a third aspect, the disclosure provides control method for full-automatic detection apparatus for important zoonotic pathogen, which includes:
  receiving a control instruction from a terminal, the control instruction includes an infectious pathogen type, an infectious pathogen detection area and a detection period;
  determining a sampling mode and a nucleic acid detection mode according to the infectious pathogen type;
  planning a target moving path and a target detection path according to the infectious pathogen detection area;
  controlling the full-automatic detection apparatus for important zoonotic pathogen to move to the infectious pathogen detection area along the target moving path;
  controlling the full-automatic detection apparatus for important zoonotic pathogen to move in the infectious pathogen detection area along the target detection path according to the detection period, and simultaneously controlling the full-automatic detection apparatus for important zoonotic pathogen to collect air according to the sampling mode;
  after the full-automatic detection apparatus for important zoonotic pathogen collects the air for the detection period, collecting a to-be-detected sample and performing nucleic acid detection on the to-be-detected sample according to the nucleic acid detection mode; and after the nucleic acid detection is completed, uploading nucleic acid detection data to the terminal.

The full-automatic detection apparatus for important zoonotic pathogen provided by the disclosure has strong practicability and can fully and continuously collect air and monitor infectious pathogens in real time, as such, it is not required to establish a professional nucleic acid detection laboratory. The full-automatic detection apparatus for important zoonotic pathogen can realize the integration of full-automatic nucleic acid detection, can be widely used in farms and disease monitoring points, and can meet monitoring and early warning requirements such as emergency monitoring and risk assessment monitoring of public emergencies.

BRIEF DESCRIPTION OF DRAWINGS

In order to explain the technical solutions of the disclosure or the related art more clearly, accompanying drawings needed to be used in the description of the embodiments or the related art will be briefly introduced below. It is apparent that the introduced accompanying drawings in the following description are some embodiments of the disclosure, and other drawings can be obtained according to these introduced drawings without creative work for ordinary skilled in the art.

FIG. 2 illustrates a flow chart of a control method full-automatic detection apparatus for important zoonotic pathogen according to an embodiment of the disclosure.

DETAILED DESCRIPTION OF EMBODIMENTS

Figure 1:
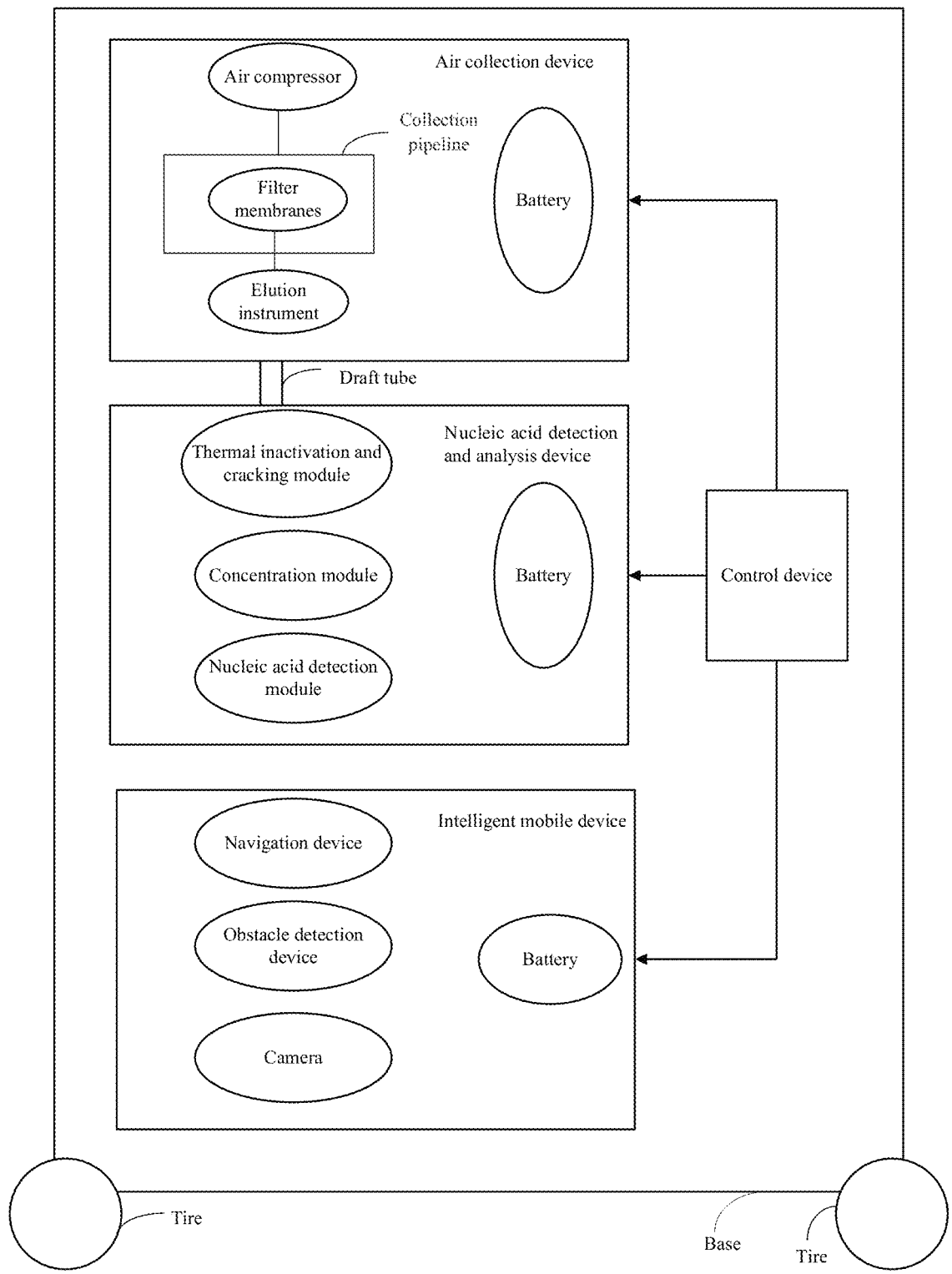
FIG. 1 illustrates a schematic structural diagram of a full-automatic detection apparatus for important zoonotic pathogen according to an embodiment of the disclosure.

In order to make objectives, technical solutions and advantages of the disclosure more clearly, the technical solutions in the disclosure will be described clearly and completely with reference to the accompanying drawings. It is apparent that the described embodiments are part of the embodiments of the disclosure, but not all of them. Based on the described embodiments in the disclosure, all other embodiments obtained by ordinary technicians in the field without creative work belong to the scope of protection of the disclosure.

In the description of the embodiments of the disclosure, it should be noted that the terms "center", "longitudinal", "lateral", "upper", "lower", "front", "rear", "left", "right", "vertical", "horizontal", "top", "bottom", "inside", "outside" and the like indicate orientations or positional relationships based on those shown in the accompanying drawings, and are intended only to facilitate description of the embodiments of the disclosure and to simplify the description, and are not intended to indicate or imply that the referenced device or element must have a particular orientation and must be constructed and operated with a particular orientation, and therefore are not to be construed as limitations on the embodiments of the disclosure. Furthermore, the terms "first", "second" and "third" are used for descriptive purposes only and are not to be understood as indicating or implying relative importance.

In the description of the embodiments of the disclosure, it is to be noted that, unless otherwise expressly specified and limited, the terms "connected" and "connecting" should be understood in a broad sense. For example, it can be fixed, detachable or integrated; it can be a mechanical connection or an electrical connection; it can be directly connected or indirectly connected through an intermediary. For those skilled in the art, the specific meanings of the above terms in the embodiments of the disclosure can be understood in specific situations.

In the embodiment of the disclosure, unless otherwise specified and limited, a first feature being "above" or "below" a second feature may mean that the first and second features are in direct contact, or the first and second features are in indirect contact through an intermediary. Moreover, the first feature being "above", "over" and "on" the second feature may mean that the first feature is directly above or obliquely above the second feature, or just means that a horizontal height of the first feature is higher than that of the second feature. The words being "under", "below" and "beneath" the first feature may mean that the first feature is directly or obliquely below the second feature, or just mean that the horizontal height of the first feature is smaller than that of the second feature.

In the description of this specification, reference to the terms "an embodiment", "some embodiments", "examples", "specific examples" or "some examples" means that specific features, structures, materials or characteristics described in connection with this embodiment or example are included in at least one embodiment or example of the embodiments of the disclosure. In this specification, schematic representations of the above terms need not be directed to the same embodiments or examples. Moreover, the specific features, structures, materials, or characteristics described may be combined in a suitable manner in any one or more of the embodiments or examples. Furthermore, without contradicting each other, those skilled in the art may combine and combine different embodiments or examples and features of different embodiments or examples described in this specification.

A full-automatic detection apparatus and system for important zoonotic pathogen, and a control method for the full-automatic detection apparatus for important zoonotic pathogen of the disclosure will be described below with reference to FIG. 1 and FIG. 2.

Based on the problems in the related art that a detection process of infectious diseases in residents' epidemic prevention areas or livestock farms is complicated, and the early warning of infectious diseases is not timely, on the one hand, please refer to FIG. 1, and the disclosure provides a full-automatic detection apparatus for important zoonotic pathogen, which includes a base, an air collection device, a nucleic acid detection and analysis device, an intelligent mobile device, and a control device. Specifically, the base is capable of moving to be arranged in any suitable position. The base may be a seat body with a tire or a track, which can move. A specific form of the base is not limited in the disclosure. The base is provided with a battery, which can be connected to other devices for power supply.

The air collection device is arranged on the base, and is configured to collect a to-be-detected sample in air along with the movement of the base. The to-be-detected sample may include at least one of bacteria, fungi, or spores. The nucleic acid detection and analysis device is arranged on the base, and is configured to detect the to-be-detected sample collected by the air collection device to determine whether an infectious pathogen exists in the to-be-detected sample. Different nucleic acid detection methods can be used by the nucleic acid detection and analysis device for different to-be-detected samples, and are not limited by the disclosure.

The intelligent mobile device is arranged on the base and electrically connected with the base, and is configured to plan and control a moving path of the base. It should be noted that the full-automatic detection apparatus can move to a target detection area by itself under the guidance of the intelligent mobile device after receiving a control instruction, and can also move in the target detection area according to a regular movement path under the control instruction and the guidance of the intelligent mobile device after moving to the target detection area, to assist the air collection device to collect air.

The control device is configured for communication connection with a terminal and is electrically connected to the intelligent mobile device, the nucleic acid detection and analysis device and the air collection device. The control device can receive a control instruction from the terminal and upload data information to the terminal. After receiving the control instruction from the terminal, the control device can first control the intelligent mobile device to plan a moving path of the base to a target sampling area according to the control instruction, and then control the intelligent mobile device to plan a sampling moving path of the base in the target sampling area after the base moves to the target sampling area. When the base moves in the target sampling area, the control device is configured to control a sampling period of the air collection device according to the control instruction, and control the nucleic acid detection and analysis device to perform nucleic acid detection after the air collection device completes collection, and transmit a detection result to the terminal.

The full-automatic detection apparatus for important zoonotic pathogen provided by the disclosure has strong practicability and can fully and continuously collect air and monitor infectious pathogens in real time, as such, it is not required to establish a professional nucleic acid detection laboratory. The full-automatic detection apparatus for important zoonotic pathogen can realize the integration of full-automatic nucleic acid detection, can be widely used in farms and disease monitoring points, and can meet monitoring and early warning requirements such as emergency monitoring and risk assessment monitoring of public emergencies.

Further, the air collection device includes an air compressor, a filter membrane and an elution instrument. The air compressor configured to extract the air along with the movement of the base. The filter membrane is configured to filter the air. The elution instrument is configured to clean the filter membrane by using a sampling medium and collect the to-be-detected sample. Specifically, the air collection device can have one or more collection pipelines, and the air compressor is connected to the one or more collection pipelines at the same time. The filter membrane is arranged in the one or more collection pipelines to filter impurities (including bacteria, viruses, spores, and dust) in the air. When a detection period is over, the elution instrument can use the sampling medium to clean the filter membrane and collect cleaned liquid to form the to-be-detected sample, the to-be-detected sample can be collected in a sampling container.

Furthermore, due to the different sizes of spores, bacteria or viruses, different filter membranes can be arranged according to different sampling requirements, and filter holes of the filter membranes have different sizes, which are used for filtering bacteria, molds, fungi, viruses and spores in the air correspondingly. Specifically, according to the detection requirements, filter membranes with different sizes can be respectively arranged in multiple collection pipelines, and the filter membranes have different aperture sizes, so as to collect one or more pathogen samples correspondingly. Alternatively, according to the detection requirements, multiple filter membranes with different sizes are arranged in one collection pipeline, pore sizes of the multiple filter membranes are different, and the multiple filter membranes are arranged in descending order of pore size, so that one pathogen sample or more pathogen samples with similar sizes can be obtained on each filter membrane. Of course, merely one filter membrane may be installed, and a pore size of the filter membrane is arranged according to the sampling requirements, which is not limited by the disclosure.

Specifically, the intelligent mobile device includes a navigation device, an obstacle detection device and a camera. The navigation module is configured to plan the moving path of the base according to a destination. The camera is configured to shoot a scene in the moving path of the base. The obstacle detection device is configured to identify an obstacle in real time according to an image shot by the camera and control the base to avoid the obstacle it should be noted that the navigation module includes two functions. One function is performing path planning from the full-automatic detection apparatus to the target detection area, which is the same as a traditional navigation function and will not be described in detail in the disclosure. Another function is performing detection path planning for the target detection area, a specific planning path can be preset, such as performing moving detection according to a regular circular route, or performing moving detection according to a S-shaped route, or performing irregular moving detection by moving to different random coordinates continuously according to a random coordinate generation mode. It should be noted that when the target detection area is small, for example, within 50 square meters, the regular circular route or S-shaped route can be used for movement detection, and when the target detection area is large, for example, more than 50 square meters, the random coordinate generation mode is preferably used for movement detection, so as to conduct more comprehensive air sampling in this area.

Further, the nucleic acid detection and analysis device includes a thermal inactivation and cracking module, a concentration module and a nucleic acid detection module. The thermal inactivation and cracking module is configured to inactivate and crack bacteria or viruses in the to-be-detected sample. The concentration module is configured to concentrate the to-be-detected sample. In the disclosure, a sampling reagent may be used for cleaning the filter membrane, the sample is liquid, and the concentration of the liquid can be specifically carried out by evaporation concentration or liquid reagent replacement purification. The nucleic acid detection module is configured to detect and determine whether the infectious pathogen exists in the to-be-detected sample. Specifically, the nucleic acid detection module is at least two in number, and detection methods used by the at least two nucleic acid detection modules include fluorescence quantification, loop-mediated isothermal amplification reaction, strand displacement isothermal amplification reaction, rolling loop amplification reaction, cross primer amplification, or recombinant polymerase isothermal amplification reaction. In practical application, corresponding nucleic acid analysis instruments and kits can be provided according to actual monitoring requirements, and one nucleic acid analysis or multiple nucleic acid analysis can be performed once, which is not limited by the disclosure. In this embodiment, the air collection device is connected to the nucleic acid detection and analysis device through a draft tube.

Based on the full-automatic detection apparatus for important zoonotic pathogen, the disclosure provides a full-automatic detection system for important zoonotic pathogen, which includes: a terminal; and at least one full-automatic detection apparatus for important zoonotic pathogen, which is electrically connected to the terminal. The full-automatic detection system for important zoonotic pathogen may include multiple full-automatic detection apparatus for important zoonotic pathogen, which can be placed in specific locations; when pathogen detection is needed, all of the multiple full-automatic detection apparatus for important zoonotic pathogen are uniformly prepared by the terminal, and can go to different areas to detect different pathogens according to corresponding instructions.

Further, referring to FIG. 2, the disclosure provides a control method for full-automatic detection apparatus for important zoonotic pathogen, which includes:

S100, receiving a control instruction from a terminal, the control instruction includes an infectious pathogen type, an infectious pathogen detection area and a detection period;

S200, determining a sampling mode and a nucleic acid detection mode according to the infectious pathogen type;

S300, planning a target moving path and a target detection path according to the infectious pathogen detection area;

S400, controlling the full-automatic detection apparatus for important zoonotic pathogen to move to the infectious pathogen detection area along the target moving path;

S500, controlling the full-automatic detection apparatus for important zoonotic pathogen to move in the infectious pathogen detection area along the target detection path according to the detection period, and simultaneously controlling the full-automatic detection apparatus for important zoonotic pathogen to collect air according to the sampling mode;

S600, after the full-automatic detection apparatus for important zoonotic pathogen collects the air for the detection period, collecting a to-be-detected sample and performing nucleic acid detection on the to-be-detected sample according to the nucleic acid detection mode; and S700, after the nucleic acid detection is completed, uploading nucleic acid detection data to the terminal.

Specifically, taking the detection of brucellosis pathogen in a livestock farm as an example, after receiving an instruction from the terminal, the full-automatic detection apparatus determines that a target detected infectious agent (i.e., infectious pathogen type) is brucellosis pathogen, and an detection area (i.e., infectious pathogen detection area) is sheep barn No. 1 with an area of 50 square meters, and a detection period is 2 hours. According to the above instruction, pore sizes of filter membranes are determined to be 0.45 micrometers (μm) (for removing large particles such as dust in the air) and 0.22 μm (for collecting brucellosis pathogen), and a nucleic acid detection mode is determined as fluorescence quantitative (PCR).

Firstly, based on the intelligent mobile device, a path of moving to the sheep barn No. 1 is planned. After moving to the sheep barn No. 1, a moving path is planned according to the area of the sheep barn No. 1, and the moving path is determined to be a circular path around a periphery of the sheep barn No. 1, and the full-automatic detection apparatus is controlled to perform sampling while moving.

After the sampling is completed, the filter membranes are washed to obtain a to-be-detected sample, and nucleic acid detection is performed on the to-be-detected sample according to the nucleic acid detection mode, and a result is uploaded to the terminal after the nucleic acid detection is completed.

Further, taking the detection of anthrax in an epidemic area as an example, after receiving an instruction from the terminal, the full-automatic detection apparatus determines that a target detected infectious agent (i.e., infectious pathogen type) is anthrax, and an detection area (i.e., infectious pathogen detection area) is residential building No. 1 with an area of 1000 square meters, and a detection period is 5 hours. According to the above instruction, pore sizes of filter membranes are determined to be 0.45 micrometers (μm) (for removing large particles such as dust in the air) and 0.22 μm (for collecting anthrax), and a nucleic acid detection mode is determined as PCR.

Firstly, based on the intelligent mobile device, a path of moving to the residential building No. 1 is planned. After moving to the residential building No 1, a moving path is planned according to the area of the residential building No. 1, and the moving path is determined to be random coordinate point movement detection, and the full-automatic detection apparatus is controlled to perform sampling while moving.

After the sampling is completed, the filter membranes are washed to obtain a to-be-detected sample, and nucleic acid detection is performed on the to-be-detected sample according to the nucleic acid detection mode, and a result is uploaded to the terminal after the nucleic acid detection is completed.

It should be noted that the result of nucleic acid detection generally need to wait for a period of time. Except that the full-automatic detection apparatus for important zoonotic pathogen needs to remain still during the process of washing and collecting samples, the full-automatic detection apparatus for important zoonotic pathogen can still accept instructions form the terminal to continue sampling or go to the next detection point for sampling within the time range of nucleic acid detection. It should also be noted that only one pathogen is detected in the two embodiments provided by the disclosure, however, multiple pathogens can be detected at the same time in the practical application process, only the pore sizes of the filter membranes and the nucleic acid detection mode need to be determined according to the detection requirements.

Finally, it should be explained that the above embodiments are merely used to illustrate the technical solutions of the disclosure, but not intended to limit thereto. Although the disclosure has been described in detail with reference to the foregoing embodiments, those skilled in the art should understand that it is still possible to modify the technical solutions described in the foregoing embodiments, or to replace some technical features with equivalents. However, these modifications or substitutions do not make the essence of the corresponding technical solutions deviate from the spirit and scope of the technical solutions of various embodiments of the disclosure.

What is claimed is:

1. A fully automatic detection apparatus for zoonotic pathogen detection, the apparatus comprising:
    a base capable of moving and comprising a tire;
    an air collection device, arranged on the base and configured to collect a to-be-detected sample in air during movement of the base, wherein the air collection device comprises multiple filter membranes, filter holes of each of the multiple filter membranes have different sizes and each of the multiple filter membranes is configured to filter one selected from the group consisting of bacteria, molds, fungi, viruses and spores of the to-be-detected sample in the air;

a nucleic acid detection and analysis device, arranged on the base and connected to the air collection device through a draft tube; wherein the nucleic acid detection and analysis device is configured to receive the to-be-detected sample from the air collection device through the draft tube and detect the to-be-detected sample to determine whether an infectious pathogen exists in the to-be-detected sample to obtain a detection result, wherein the nucleic acid detection and analysis device comprises multiple nucleic acid detection modules for determining whether the infectious pathogen exists in the to-be-detected sample;

a mobile device, arranged on the base and electrically connected to the base, wherein the mobile device comprises a navigation device, an obstacle detection device and a camera connected to the obstacle detection device, the navigation device is configured to receive, from a control device, a control instruction from a terminal and plan a target moving path and a target detection path of the base according to the control instruction, and the obstacle detection device is configured to, based on an image shot by the camera, detect an obstacle in the target moving path and control the base to avoid the obstacle, wherein the obstacle is an object that hinders the base from moving in target moving path; and the control device, wherein the control device is configured for communication connection with the terminal and is electrically connected to the mobile device, the nucleic acid detection and analysis device and the air collection device; and the control device is configured to receive the control instruction from the terminal and further configured, according to the control instruction, to determine a target filter membrane for collecting the to-be-detected sample of the multiple filter membranes, a target nucleic acid detection module for detecting the to-be-detected sample of the nucleic acid detection modules and sampling time for sampling the to-be-detected sample, and the control device is configured to: transmit the control instruction to the mobile device to make the mobile device plan the target moving path and the target detection path of the base; and receive and transmit the detection result from the nucleic acid detection and analysis device to the terminal; wherein the target moving path is a path along which the base moves from a current position of the base to a target detection area, and the target detection path is a path along which the base moves in the target detection area; and the target detection path is a circular route or an S-shaped route;

wherein the control instruction comprises an infectious pathogen type, the target detection area and a detection period.

2. The fully automatic detection apparatus for zoonotic pathogen detection as claimed in claim 1, wherein the air collection device comprises:

a collection pipeline;

an air compressor, connected to the collection pipeline and configured to extract the air during the movement of the base to make the air enter the collection pipeline;

the multiple filter membranes, disposed in the collection pipeline and configured to filter the air; and an elution instrument, connected to the multiple filter membranes and configured to clean the target filter membrane to collect the to-be-detected sample.

3. A fully automatic detection method for zoonotic pathogen detection, implemented by the fully automatic detection apparatus for zoonotic pathogen detection as claimed in claim 1, the method comprising:

receiving, by the control device, the control instruction from the terminal;

determining, by the control device, the target filter membrane and the target nucleic acid detection module according to the infectious pathogen type of the control instruction;

planning, by the navigation device, the target moving path and the target detection path according to the target detection area of the control instruction;

controlling, by the control device, the fully automatic detection apparatus for zoonotic pathogen detection to move to the target detection area along the target moving path;

controlling, by the control device, the fully automatic detection apparatus for zoonotic pathogen to move in the target detection area along the target detection path for the detection period, and controlling, by the control device, the fully automatic detection apparatus for zoonotic pathogen detection to collect the air by using the target filter membrane;

after the fully automatic detection apparatus for zoonotic pathogen detection collects the air for the detection period, collecting, by the target filter membrane, the to-be-detected sample and performing, by the target nucleic acid detection module, nucleic acid detection on the to-be-detected sample to obtain the detection result; and after the nucleic acid detection is completed, uploading, by the control device, the detection result to the terminal.

* * * * *